(12) United States Patent
Ji et al.

(10) Patent No.: US 9,498,178 B2
(45) Date of Patent: Nov. 22, 2016

(54) METHOD FOR SPECTRAL CT LOCAL TOMOGRAPHY

(71) Applicant: TOSHIBA MEDICAL SYSTEMS CORPORATION, Otawara-shi (JP)

(72) Inventors: Changguo Ji, Vernon Hills, IL (US); Yuexing Zhang, Naperville, IL (US); Xiaolan Wang, Buffalo Grove, IL (US); Daniel Gagnon, Twinsburg, OH (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/990,636

(22) Filed: Jan. 7, 2016

(65) Prior Publication Data

US 2016/0113613 A1 Apr. 28, 2016

Related U.S. Application Data

(62) Division of application No. 14/063,008, filed on Oct. 25, 2013, now Pat. No. 9,274,066.

(51) Int. Cl.
*G01N 23/04* (2006.01)
*A61B 6/00* (2006.01)
*A61B 6/03* (2006.01)

(52) U.S. Cl.
CPC ............ *A61B 6/5205* (2013.01); *A61B 6/032* (2013.01); *A61B 6/4014* (2013.01); *A61B 6/4241* (2013.01); *A61B 6/4266* (2013.01); *A61B 6/469* (2013.01); *A61B 6/482* (2013.01); *G01N 23/046* (2013.01)

(58) Field of Classification Search
CPC ............................ A61B 6/482; A61B 6/4035
See application file for complete search history.

(56) References Cited

U.S. PATENT DOCUMENTS

| | | |
|---|---|---|
| 2008/0056435 A1 | 3/2008 | Basu |
| 2011/0096892 A1 | 4/2011 | Forthmann |
| 2012/0069953 A1* | 3/2012 | Chandra .................. A61B 6/03 378/5 |
| 2013/0251097 A1 | 9/2013 | Zou |
| 2013/0343517 A1 | 12/2013 | Gagnon et al. |
| 2014/0233694 A1 | 8/2014 | Wang |
| 2014/0241489 A1 | 8/2014 | Zhang |
| 2014/0270056 A1 | 9/2014 | Zou |
| 2015/0223766 A1 | 8/2015 | Besson |

FOREIGN PATENT DOCUMENTS

JP 2014-4373 A 1/2014

\* cited by examiner

*Primary Examiner* — Hoon Song
(74) *Attorney, Agent, or Firm* — Oblon, McClelland, Maier & Neustadt, L.L.P.

(57) ABSTRACT

A method for performing reconstruction for a region of interest (ROI) of an object is provided. The method includes designating the ROI within the object, the ROI being located within a scan field of view (FOV) of a combined third- and fourth-generation CT scanner, the CT scanner including fixed photon-counting detectors (PCDs), and an X-ray source that rotates about the object in synchronization with a rotating detector. Further, the method includes determining, for each PCD, as a function of view angle, an on/off timing schedule, based on a size and location of the designated ROI, and performing a scan to obtain a first data set from the rotating detector and a second data set from the plurality of PCDs, while turning each PCD on and off according to the determined schedule. Finally, the method includes performing reconstruction using the first and second data sets to obtain ROI spectral images.

11 Claims, 12 Drawing Sheets

METHOD FOR SPECTRAL CT LOCAL TOMOGRAPHY

CROSS-REFERENCE TO RELATED APPLICATIONS

This application is a divisional application of U.S. application Ser. No. 14/063,008, filed Oct. 25, 2013, the entire contents of which are incorporated herein by reference.

FIELD

Embodiments disclosed herein generally relate to methods for computed tomography (CT) imaging. In particular, embodiments disclosed herein relate to an apparatus and an associated method for spectral CT reconstruction for one or more regions of interest.

BACKGROUND

Radiographic imaging, in its simplest expression, is an X-ray beam traversing an object and a detector relating the overall attenuation per ray. The attenuation is derived from a comparison of the same ray with and without the presence of the object. From this conceptual definition, several aspects are required to properly construct an image in 3D. For instance, the finite size of the X-ray focal spot, the nature and shape of the filter blocking the very low-energy X-ray from the tube, the details of the geometry and characteristics of the detector and the capacity of the data acquisition system are all elements that affect how the actual reconstruction is performed.

CdTe/CZT-based photon-counting detectors suffer from polarization upon irradiation by non- or low-attenuated beams near the edges of the scan field of view (FOV) and/or after scanning low-attenuation regions of the patient, e.g., the lung. Dynamic (mechanical) bowtie filters or collimators that attempt to attenuate such beams to compensate for the variations in patient size and shape is not feasible due to fast CT gantry rotation speeds, high centrifugal forces on the gantry rotating base, and system reliability challenges.

BRIEF DESCRIPTION OF THE DRAWINGS

A more complete appreciation of the disclosed embodiments and many of the attendant advantages thereof will be readily obtained as the same becomes better understood by reference to the following detailed description when considered in connection with the accompanying drawings, wherein.

DETAILED DESCRIPTION

Figure 1:
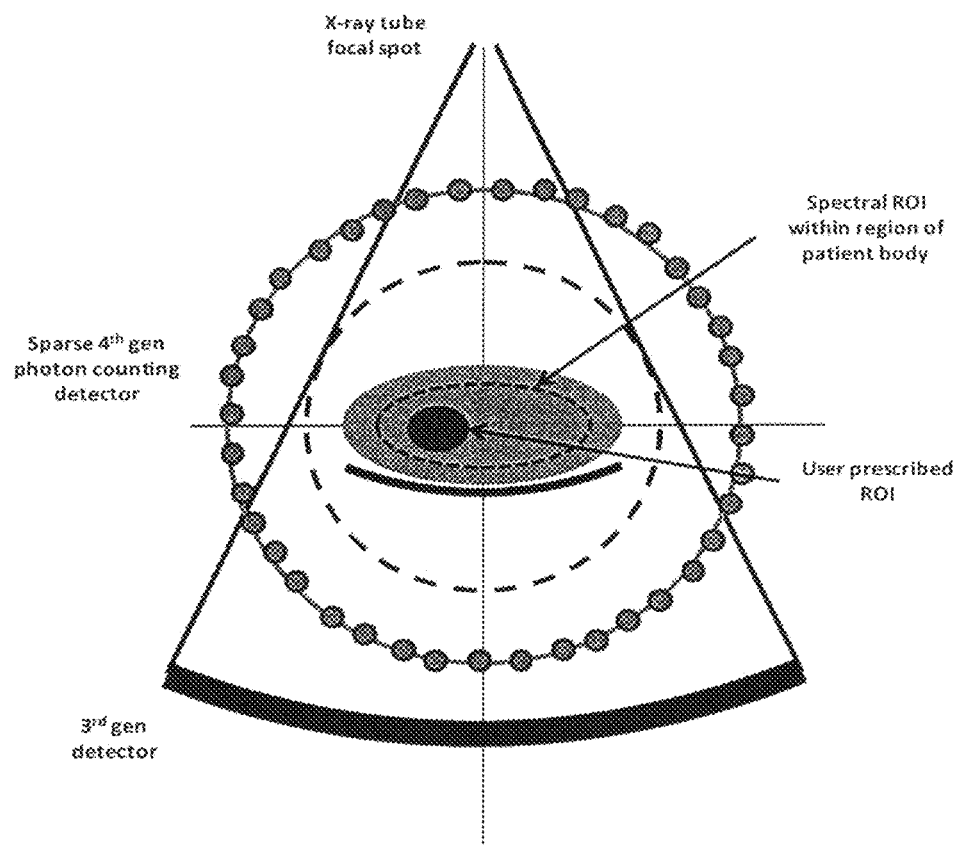
FIG. 1 illustrates a combined third-fourth-generation CT scanner according to one embodiment.

Embodiments disclosed herein relate to methods for performing spectral reconstruction of a region of interest of an object using various CT scanner architectures.

In particular, in one embodiment, there is provided a method of performing spectral reconstruction for a region of interest (ROI) of an object, the method comprising: (1) designating the ROI within the object, the ROI being located within a scan field of view (FOV) of a combined third- and fourth-generation computed tomography (CT) scanner, the CT scanner including a plurality of fixed photon-counting detectors (PCDs), and an X-ray source that rotates in a trajectory about the object in synchronization with an energy-integrating detector; (2) determining, for each PCD of the plurality of PCDs, as a function of a position of the X-ray source along the trajectory, an on/off timing schedule of the PCD, based on a size and location of the designated ROI, (3) performing a scan of the object by rotating the X-ray source and the energy-integrating detector to obtain a first data set from the energy-integrating detector and a second data set from the plurality of PCDs, wherein the step of performing the scan includes turning each PCD on and off according to the determined on/off timing schedule of the PCD; and (4) performing spectral reconstruction within the ROI using the first and second data sets to obtain spectral images of the ROI.

In one embodiment, the step of performing reconstruction further comprises generating a full energy-integrating image within the scan FOV.

In another embodiment, the step of performing the scan comprises turning each PCD on and off by controlling a bias voltage of the PCD.

In another embodiment, the designating step comprises: (1) obtaining a scout scan of the object; and (2) receiving designation of the ROI from a user input device, based on the scout scan.

In another embodiment, there is provided an apparatus for performing spectral reconstruction for a region of interest (ROI) of an object, the apparatus being communicatively connected to a combined third- and fourth-generation computed tomography (CT) scanner, the CT scanner including a plurality of fixed photon-counting detectors (PCDs), and an X-ray source that rotates in a trajectory about the object in synchronization with an energy-integrating detector, the apparatus comprising a circuit configured to (1) receive designation of the ROI within the object, the ROI being located within a scan field of view (FOV) of the CT scanner; (2) determine, for each PCD of the plurality of PCDs, as a function of a position of the X-ray source along the trajectory, an on/off timing schedule of the PCD, based on a size and location of the designated ROI; (3) cause the CT scanner to perform a scan of the object by rotating the X-ray source and the energy-integrating detector to obtain a first data set from the energy-integrating detector and a second data set from the plurality of PCDs, wherein circuit is further configured to send signals to the CT scanner to turn each PCD on and off according to the determined on/off timing schedule of the PCD; and (4) perform spectral reconstruction within the ROI using the first and second data sets to obtain spectral images of the ROI.

In another embodiment, there is provided a CT scanner for performing spectral reconstruction for a region of interest (ROI) of an object, the apparatus comprising: (1) a combined third- and fourth-generation computed tomography (CT) scanner, the CT scanner including a plurality of fixed photon-counting detectors (PCDs), and an X-ray source that rotates in a trajectory about the object in synchronization with an energy-integrating detector; and 92) a circuit configured to (a) receive designation of the ROI within the object, the ROI being located within a scan field of view (FOV) of the CT scanner; (b) determine, for each PCD of the plurality of PCDs, as a function of a position of the X-ray source along the trajectory, an on/off timing schedule of the PCD, based on a size and location of the designated ROI; (c) cause the CT scanner to perform a scan of the object by rotating the X-ray source and the energy-integrating detector to obtain a first data set from the energy-integrating detector and a second data set from the plurality of PCDs, wherein circuit is further configured to send signals to the CT scanner to turn each PCD on and off according to the determined on/off timing schedule of the PCD; and (d) perform spectral reconstruction within the ROI using the first and second data sets to obtain spectral images of the ROI.

In another embodiment, there is provided a method of performing spectral reconstruction for a region of interest (ROI) of an object, the method comprising: (1) designating the ROI within the object, the ROI being located within a scan field of view (FOV) of a computed tomography (CT) scanner having an X-ray source; (2) performing a first scan of the object using a first peak voltage of the X-ray source and a first filter, to obtain a first data set, the first filter corresponding to the scan FOV; (3) performing a second scan of the object using a second peak voltage of the X-ray source and a second filter, to obtain a second data set, the second filter resulting in a FOV corresponding to the ROI; and (4) performing spectral reconstruction within the ROI using the first and second data sets to obtain spectral images of the ROI.

In another embodiment, the method included switching from the first filter to the second filter after the first scan but before the second scan, wherein the first and second filters are bowtie filters.

In another embodiment, there is provided an apparatus for performing spectral reconstruction for a region of interest (ROI) of an object, the apparatus being communicatively connected to a computed tomography (CT) scanner having an X-ray source, the apparatus comprising a circuit configured to (1) receive designation of the ROI within the object, the ROI being located within a scan field of view (FOV) of the computed tomography (CT) scanner; (2) cause the CT scanner to perform a first scan of the object using a first peak voltage of the X-ray source and a first filter, to obtain a first data set, the first filter corresponding to the scan FOV; (3) cause the CT scanner to perform a second scan of the object using a second peak voltage of the X-ray source and a second filter, to obtain a second data set, the second filter resulting in a FOV corresponding to the ROI; and (4) perform spectral reconstruction within the ROI using the first and second data sets to obtain spectral images of the ROI.

In another embodiment, there is provided a method of performing spectral reconstruction for a region of interest (ROI) of an object, the method comprising: (1) designating the ROI within the object, the ROI being located within a scan field of view (FOV) of a dual-source, dual detector computed tomography (CT) scanner, the CT scanner having a first X-ray source and a second X-ray source; (2) setting a first peak voltage and a first FOV for the first X-ray source; (3) setting a second peak voltage and a second FOV for the second X-ray source, the second FOV corresponding to the ROI; (4) performing a scan of the object using the first and second X-ray sources to obtain first and second data sets, respectively; and (5) performing spectral reconstruction within the ROI using the first and second data sets to obtain spectral images of the ROI.

In one embodiment, the CT scanner includes a first detector and a second detector, and the first and second detectors have different sizes.

In another embodiment, there is provided an apparatus for performing spectral reconstruction for a region of interest (ROI) of an object, the apparatus being communicatively connected to a dual-source, dual detector computed tomography (CT) scanner, the CT scanner having a first X-ray source and a second X-ray source, the apparatus comprising a circuit configured to (1) receive designation of the ROI within the object, the ROI being located within a scan field of view (FOV) of the dual-source, dual detector CT scanner; (2) set a first peak voltage and a first FOV for the first X-ray source; (3) set a second peak voltage and a second FOV for the second X-ray source, the second FOV corresponding to the ROI; (4) cause the CT scanner to perform a scan of the object using the first and second X-ray sources to obtain first and second data sets, respectively; and (5) perform spectral reconstruction within the ROI using the first and second data sets to obtain spectral images of the ROI.

$3^{rd}/4^{th}$ Generation Architecture

FIG. 1 illustrates a combined third and spectral fourth-generation CT scanner, which includes an X-ray tube and a first detector that rotate together, along with a second, stationary detector formed of sparse, photon-counting detector (PCD) elements. In one embodiment, the first detector includes conventional energy-integrating (EI) detector elements.

Figure 2:
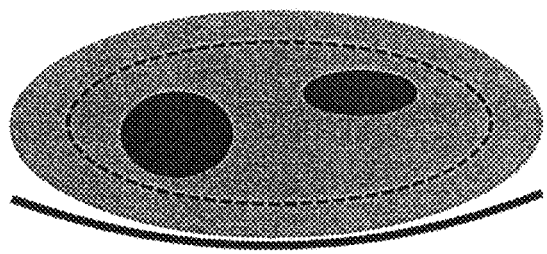
FIG. 2 illustrates designation of one or more regions of interest (ROIs) within an object.

As shown in FIGS. 1 and 2, within the spectral region of interest (ROI), a user can prescribe one or more smaller ROIs, having various sizes and aspect ratios, for spectral imaging, based on scout scans. The user-prescribed ROIs are within the regions of the patient where the X-ray beam is attenuated by a bowtie filter and the patient body to levels that are appropriate for PCDs. In addition, the location, shape, and size of a user-prescribed ROI can vary in the z-direction for volume axial or helical scans.

Prior to the scan, based on the location of the user-prescribed ROI(s) and various scan parameters, a system controller calculates an ON/OFF timing schedule to be used during the scan for each of the sparse fourth generation PCDs. During the scan, energy-integrating data is collected by the first detector for the full FOV with the third-generation system. In addition, truncated spectral data (for the user-prescribed ROIs only) is collected by the sparse fourth-generation PCDs. Note that, during the scan, the system controller turns each PCD ON and OFF with the respective bias voltage, based on the predetermined ON/OFF timing schedule.

Figure 3:
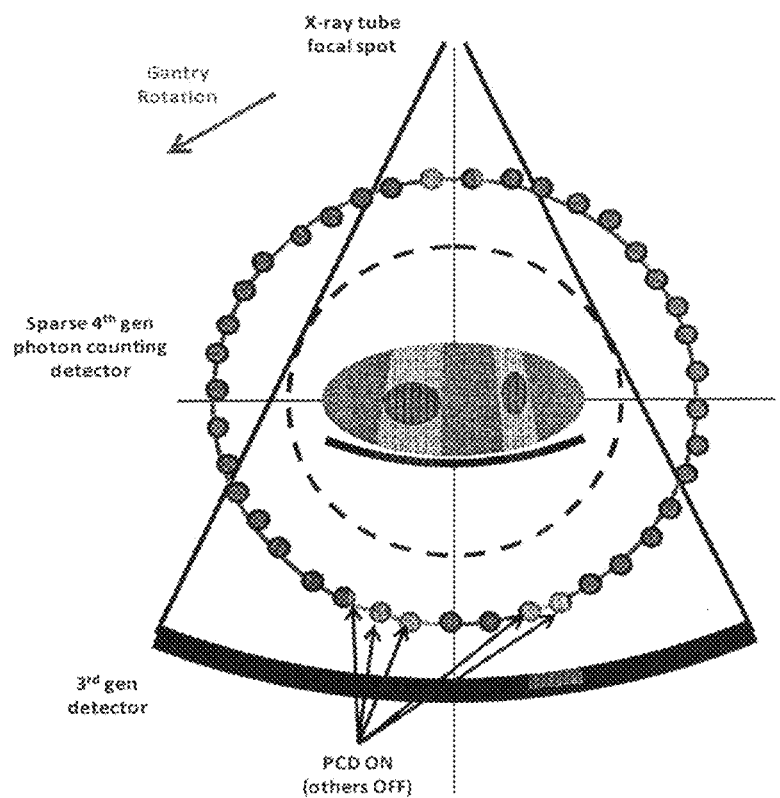
FIGS. 3 and 4 illustrates a combined third-fourth-generation CT scanner in which PCDs are turned on and off based on the size and location of the ROIs.
Figure 4:
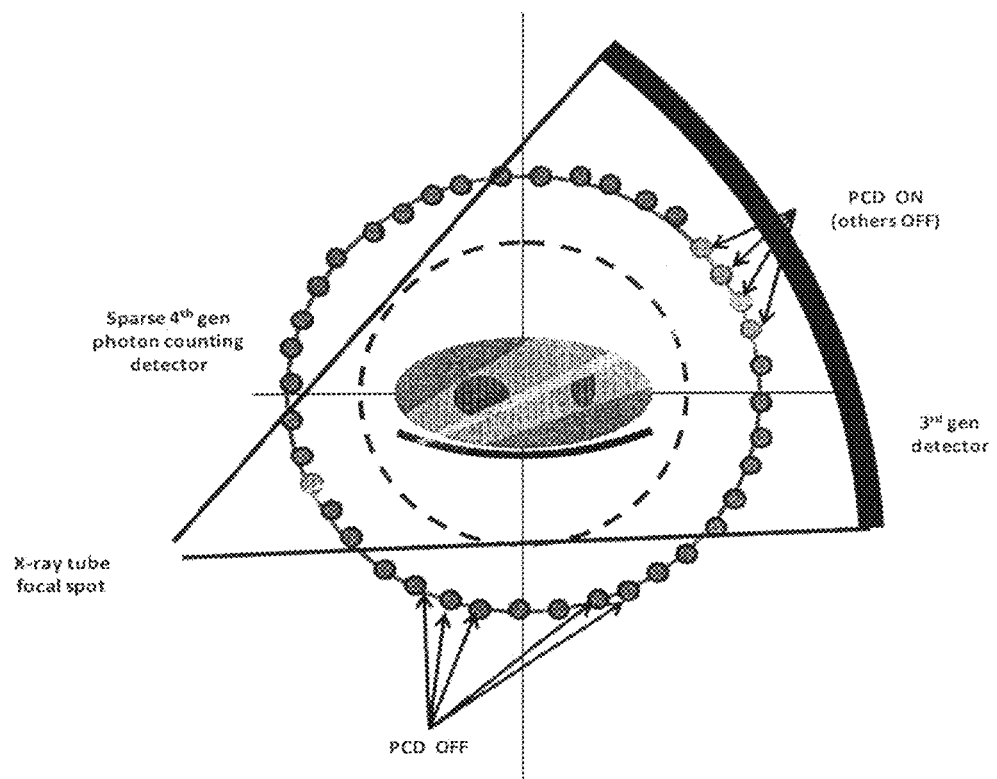

FIGS. 3 and 4 illustrate examples of the fixed, sparse PCDs being turned ON and OFF as the X-ray source rotates, based on the size and location of the one or more user-prescribed ROIs. Note that, as shown in FIGS. 4 and 5, a given PCD can be OFF or ON depending on the location of the X-ray source during the scan.

Figure 5:
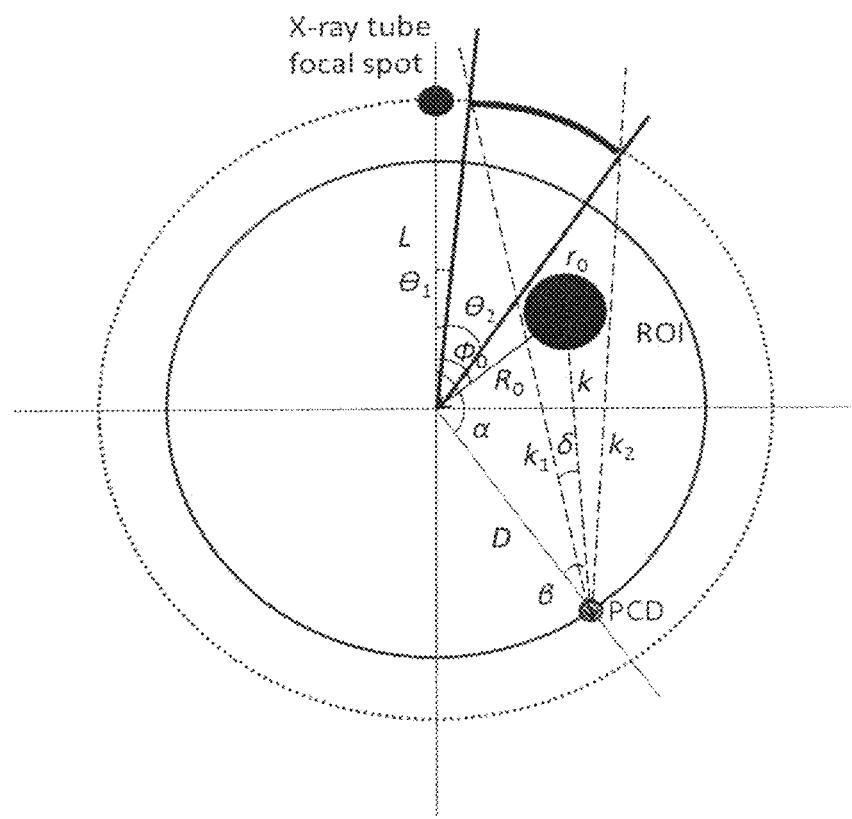
FIG. 5 illustrates a method for determining whether a given PCD should be on or off based on a given ROI and X-ray source position, according to one embodiment.

FIG. 5 is a diagram for explaining how the system controller determines when to turn each PCD ON or OFF during the scan based on the scanner geometry and the location of a user-prescribed ROI. The "PCD ON" period for a PCD and a given ROI can be described in terms of the X-ray tube position, i.e., view number.

In this example, the illustrated PCD is fixed at a distance D from the isocenter, at angular position $\alpha$ relative to the CT gantry. Further, the illustrated ROI is round and has a radius of $r_0$ and a center at a distance $R_0$ from the isocenter, with a center angular position of $\Phi_0$ (relative to the CT gantry). Thus, for an X-ray tube with focal spot rotating around the isocenter at a radius L, the angular range (view #s) of the tube corresponding to the ROI for the given PCD can be calculated as follows (in terms of $\theta_1$ and $\theta_2$):

$$k = \sqrt{R_0^2 + D^2 - 2R_0 D \cos(\alpha - \Phi_0)}$$

$$\delta = \sin^{-1} \frac{r_0}{k}$$

$$\beta = \cos^{-1} \frac{D^2 + k^2 - R_0^2}{2Dk}$$

$$k_1 = D\cos(\beta - \delta) + \sqrt{L^2 - D^2 \sin^2(\beta - \delta)}$$

$$k_2 = D\cos(\beta + \delta) + \sqrt{L^2 - D^2 \sin^2(\beta + \delta)}$$

$$\theta_1 = \alpha - \cos^{-1} \frac{k_1^2 - L^2 - D^2}{2DL}$$

$$\theta_2 = \alpha - \cos^{-1} \frac{k_2^2 - L^2 - D^2}{2DL}$$

The angles $\theta_1$ and $\theta_2$ determine the view numbers for the PCD ON state for the given PCD. The calculation for each of the other PCDs is similar.

After the scan, the full-view energy-integrating data and the truncated spectral data are used for reconstruction within the user-prescribed ROIs. An example of such a reconstruction algorithm is the compressive sensing-based statistical interior tomography method (CS-SIT). The reconstruction process generates both the full EI image within the scan FOV and spectral images within the user-prescribed ROIs, which are displayed to the user.

Note that an advantage of this embodiment is that ROIs can be easily defined so that a variable portion of the object can be imaged, while protecting the PCD detector elements from the high flux of an unobstructed beam.

Figure 11:
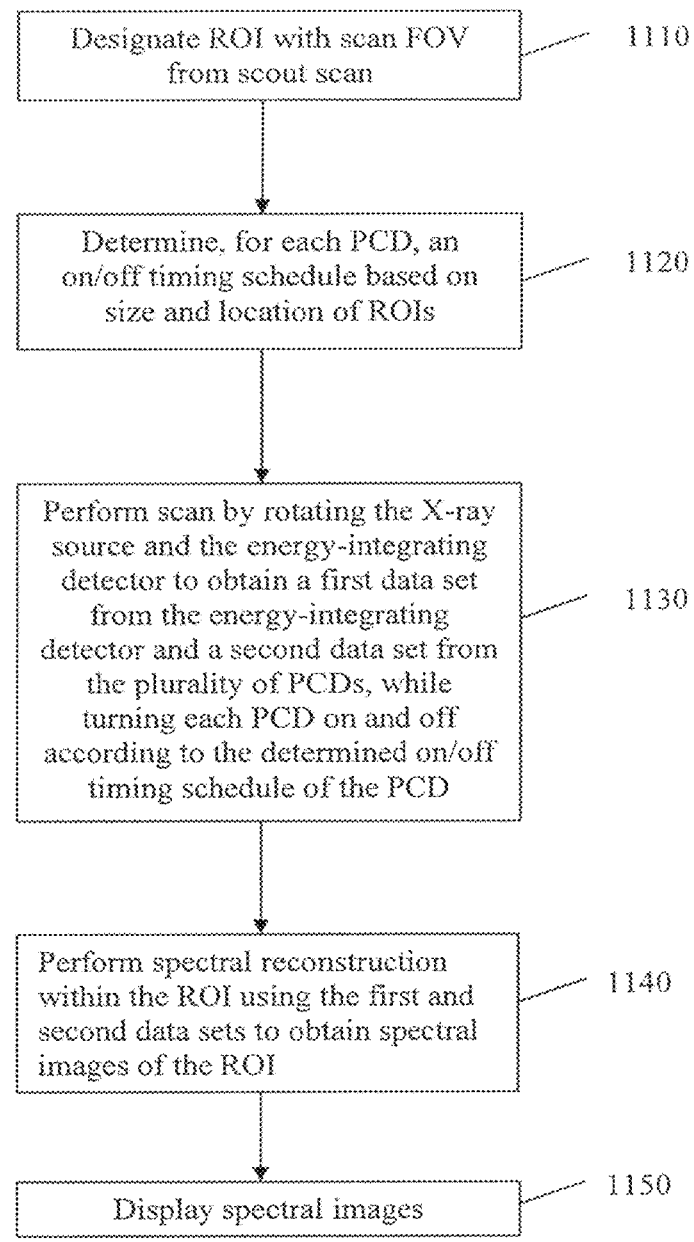
FIG. 11 illustrates a method of performing spectral reconstruction of an ROI with a combined third- and fourth-generation CT scanner.

FIG. 11 shows a flowchart that describes a method according to one embodiment.

In particular, in step 1110, the operator designates one or more ROIs with the scan FOV, based, e.g., from viewing a scout scan.

In step 1120, a processor or specialized circuit determines, for each PCD, an on/off timing schedule based on size and location of the ROIs, using the process described above.

In step 1130, a scan is performed by rotating the X-ray source and the energy-integrating detector to obtain a first data set from the energy-integrating detector and a second data set from the plurality of PCDs, while turning each PCD on and off according to the determined on/off timing schedule of the PCD.

In step 1140, spectral reconstruction is performed within the ROI using the first and second data sets to obtain spectral images of the ROI.

In step 1150, the spectral images and a full EI image are displayed.

Slow-KVP Switching

In another embodiment, slow kVp (peak kilovoltage) switching is used to obtain two data sets for truncated reconstruction of one or more user-prescribed ROIs. Note that any type of scanner architecture and any type of detector elements can be used in this embodiment.

Figure 6:
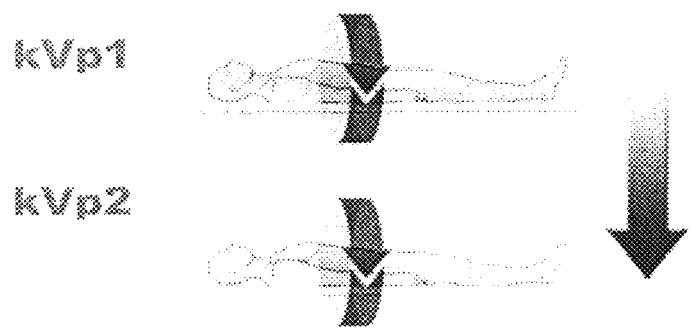
FIG. 6 illustrates slow kVp switching according to one embodiment.
Figure 7:
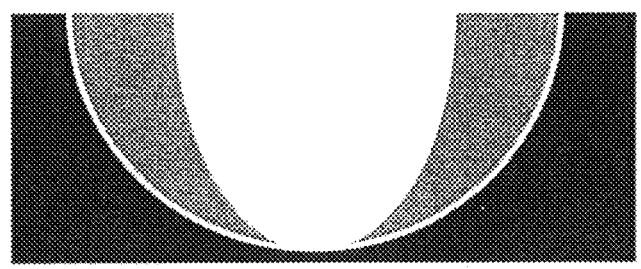
FIGS. 7 and 8 illustrate the switching between two bowtie filters according to one embodiment.
Figure 8:
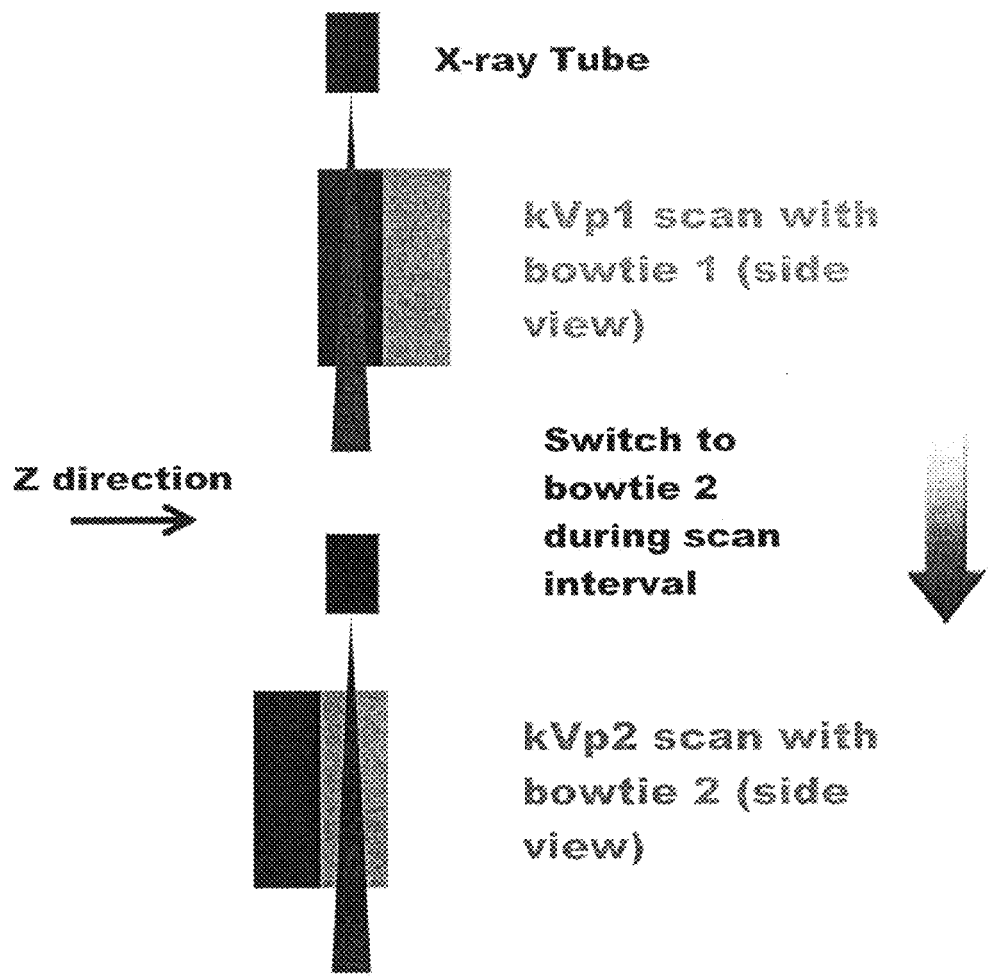

In particular, as shown in FIGS. 6-8, two bowtie filters are used to obtain two different scan FOVs. In the first scan, the large-FOV bowtie filter is used together with a first $kVp_1$ (a high kVp) to obtain a first data set.

Then, as shown in FIG. 8, the bowtie filter is switched after the first scan to obtain a smaller-FOV filter by moving the filter in the z direction. Note that the range of movement in the z direction depends upon the desired z coverage. Note also that half scans (plus DET fan angle) from behind the table can also be used to further reduce the radiation dose.

In another embodiment, the bowtie switching can be implemented by inserting an additional attenuation block onto the existing large-FOV bowtie filter to obtain the smaller-FOV bowtie filter.

Next, as shown in FIGS. 6 and 8, a second scan with the smaller-FOV bowtie filter and a second, different $kVp_2$ (a low kVp) is performed to obtain a second data set.

Next, the first data set corresponding to the large-FOV/$kVp_1$ scan and the second data set corresponding to the smaller-FOV/$kVp_2$ scan are used in a reconstruction process. In particular, the reconstruction process generates a full EI image for the large FOV and spectral images for the smaller FOV, which are displayed to the user. An advantage of this embodiment is that spectral images are obtained at a lower radiation dose.

Figure 12:
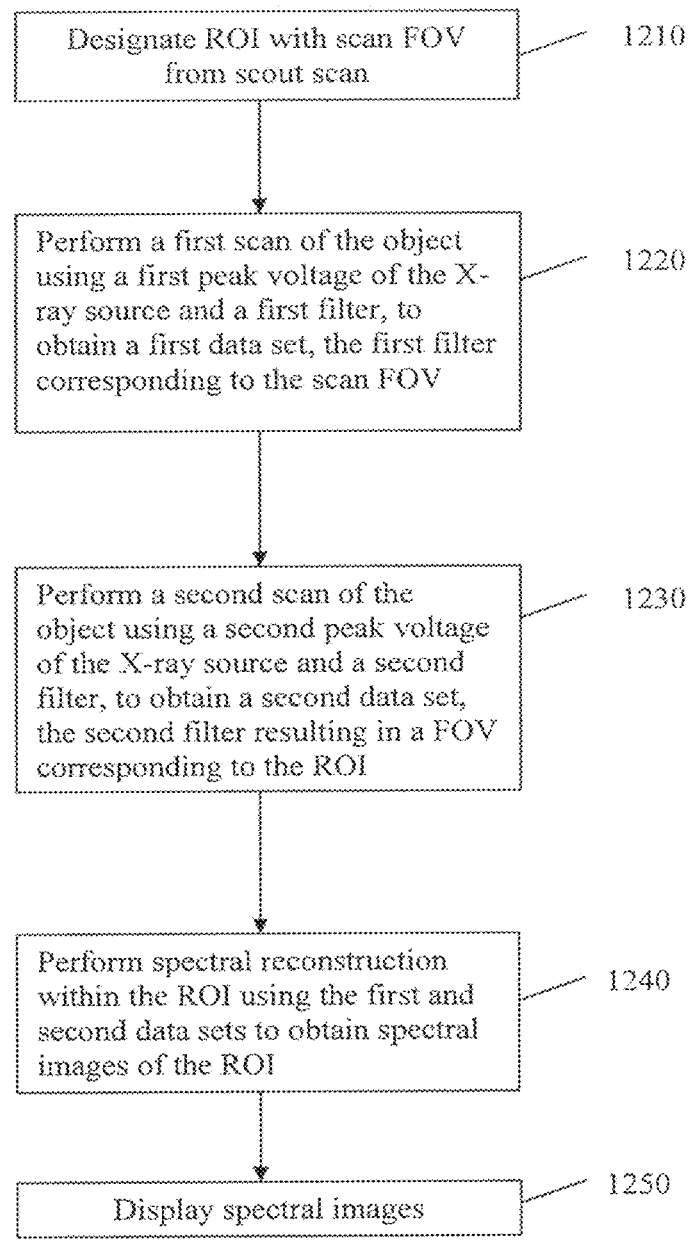
FIG. 12 illustrates a method of performing spectral reconstruction of an ROI using slow kVp switching.

FIG. 12 shows a flowchart that describes a method according to one embodiment.

In particular, in step 1210, the operator designates one or more ROIs with the scan FOV, based, e.g., from viewing a scout scan.

In step 1220, a first scan of the object is performed using a first peak voltage of the X-ray source and a first filter, to obtain a first data set, the first filter corresponding to the scan FOV.

In step 1230, a second scan of the object is performed using a second peak voltage of the X-ray source and a second filter, to obtain a second data set, the second filter resulting in a FOV corresponding to the ROI.

In step 1240, spectral reconstruction is performed within the ROI using the first and second data sets to obtain spectral images of the ROI.

In step 1250, the spectral images and a full EI image are displayed.

Dual-Source/Dual-Detector

Figure 9:
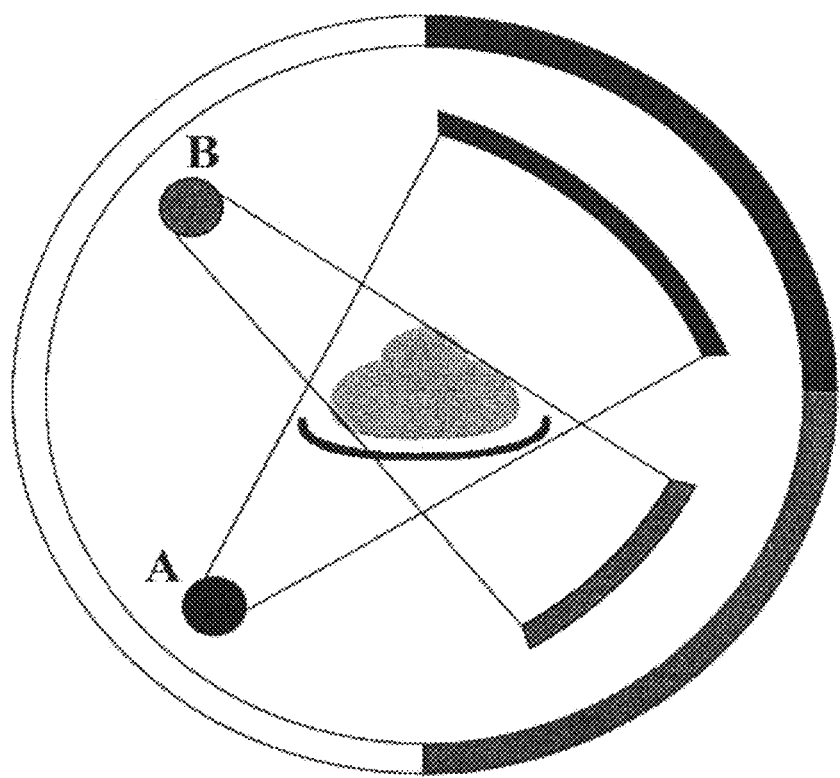
FIG. 9 illustrates a dual-source, dual-detector scanner.

In another embodiment, a dual-source, dual-detector scanner is used to obtain two data sets for truncated reconstruction of one or more user-prescribed ROIs. In this embodiment, as shown in FIG. 9, a different scan FOV and/or different detector sizes are used for the different source/detector pairs, based on the user-prescribed ROI(s). Further, a different kVp is used for the two sources during the scan, similar to the slow kVp switching embodiments, to obtain first and second data sets, respectively. For example, the first source/detector pair has a large FOV and uses $kVp_1$, while the second source/detector pair has a smaller FOV and uses $kVp_2$. In one embodiment, both detectors use EI detector elements.

Next, the first data set corresponding to the large-FOV/$kVp_1$ scan and the second data set corresponding to the smaller-FOV/$kVp_2$ scan are used in a reconstruction process. In particular, the reconstruction process generates a full EI image for the large FOV and spectral images for the smaller FOV, which are displayed to the user. An advantage of this embodiment is that spectral images are obtained at a lower radiation dose.

In an alternative embodiment, one of the detectors, or the center portion of the detectors, can be spectral detectors (e.g., photon counting, dual layer), while the rest of the detector elements can be energy-integrating detector elements. This also allows different FOVs for different detectors for dose considerations. When CdTe/CZT-based photon-counting detectors are used to collect spectral data for the smaller FOV/ROI, detector polarization is mitigated.

Figure 13:
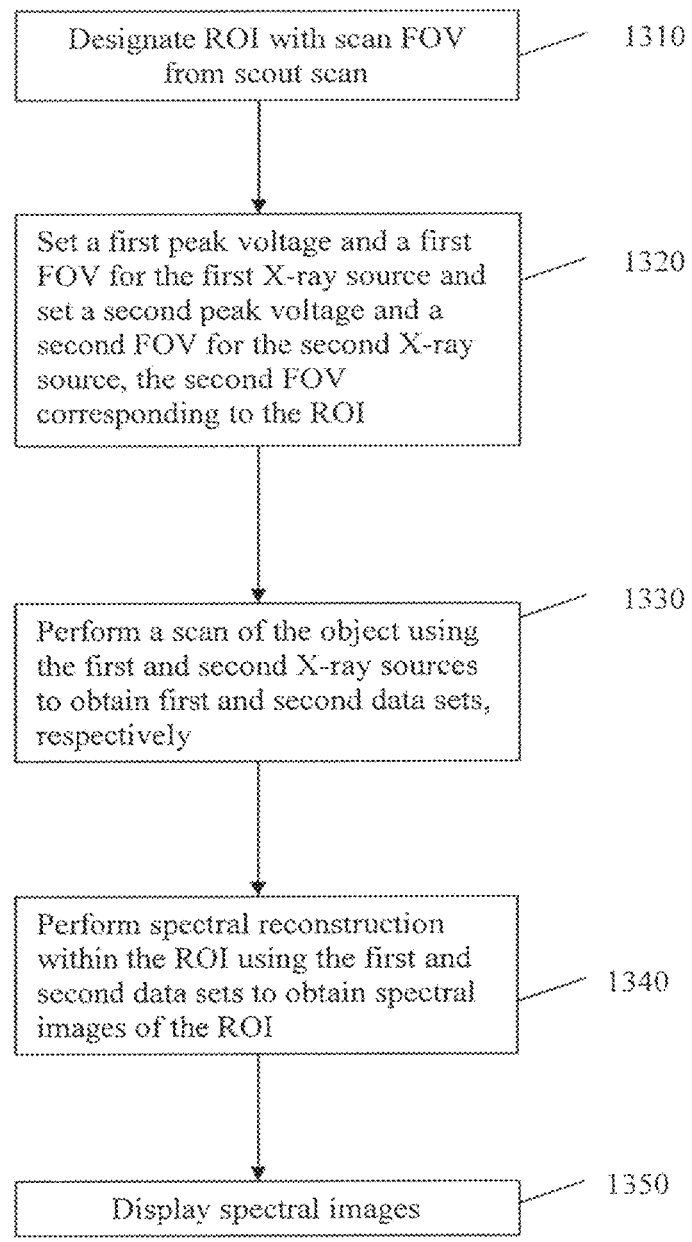
FIG. 13 illustrates a method of performing spectral reconstruction of an ROI using a dual-source, dual-energy CT scanner.

FIG. 13 shows a flowchart that describes a method according to one embodiment.

In particular, in step 1310, the operator designates one or more ROIs with the scan FOV, based, e.g., from viewing a scout scan.

In step 1320, a first peak voltage and a first FOV for the first X-ray source is set and a second peak voltage and a second FOV for the second X-ray source is set, the second FOV corresponding to the ROI.

In step 1330, a scan of the object is performed using the first and second X-ray sources to obtain first and second data sets, respectively.

In step 1340, spectral reconstruction is performed within the ROI using the first and second data sets to obtain spectral images of the ROI.

In step 1350, the spectral images and a full EI image are displayed.

Figure 10:
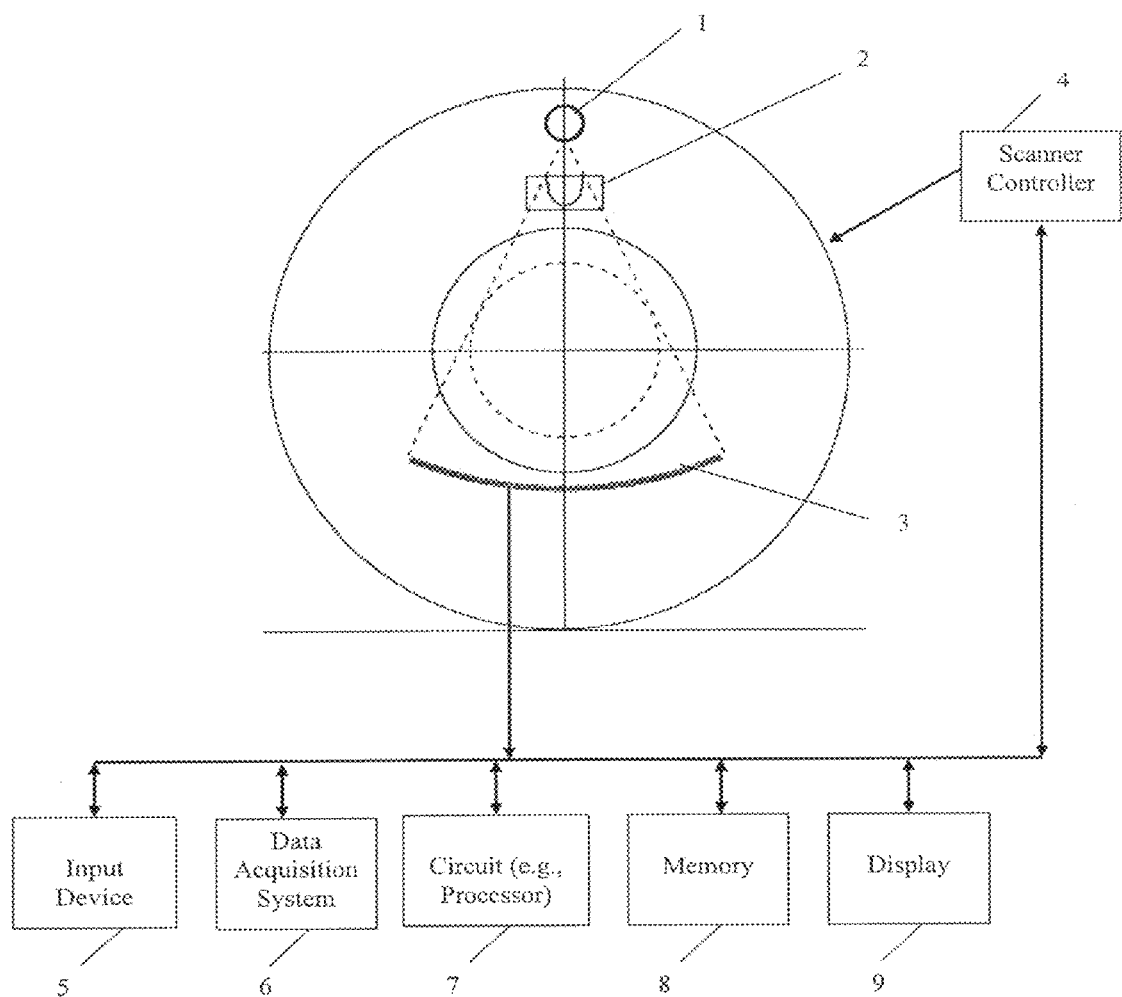
FIG. 10 illustrates a CT scanner according to one embodiment.

FIG. 10 illustrates the basic structure of a conventional third-generation CT apparatus that can be used in some of the embodiments disclosed herein. Note that similar hardware can be used in conjunction with the combined third- and fourth generation CT scanner shown in FIG. 1, as well as dual source, dual detector CT scanners described above. For example, a ring of fixed PCDs, as shown in FIG. 1, can be used in conjunction with (e.g., controlled by) the hardware shown in FIG. 10.

The CT apparatus of FIG. 10 includes an X-ray tube 1, filters and collimators 2, and a detector 3. The X-ray source and the detector can rotate in synchronization with one another. The CT apparatus will also include additional mechanical and electrical components such as a gantry motor and a scanner controller 4 to control the rotation of the gantry, control the X-ray source, and control a patient bed. The CT apparatus also includes a data acquisition system 6 to obtain projection data from the detector 3 and a circuit 7 to generate CT images based on the projection data acquired by the data acquisition system. As discussed in more detail below, the circuit 7 can be a dedicated, specialize circuit or a computer (hardware) processor, such as a microprocessor, that is configured (e.g., programmed with computer program instructions) to perform the functions disclosed above and shown in the flowcharts. The circuit 7 and the data acquisition system 6 make use of a memory 8, which is configured to store, e.g., data obtained from the detector as well as reconstructed images.

Further, the CT apparatus can include an input device 5 for receiving user input (e.g., designating a ROI), and a display 9 to display reconstructed spectral images, e.g., spectral images of the ROT.

The circuit 7 can be a hardware processor that executes software to control the scanner controller to perform a scan and to turn PCDs on an off according to a schedule determined by the circuit 7, as discussed above.

As one of ordinary skill in the art would recognize, the circuit 7 can include a CPU that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the memory may be non-volatile, such as ROM, EPROM, EEPROM or FLASH memory. The memory can also be volatile, such as static or dynamic RAM, and a processor, such as a microcontroller or microprocessor, may be provided to manage the electronic memory as well as the interaction between the FPGA or CPLD and the memory.

Alternatively, the CPU in the circuit 7 may execute a computer program including a set of computer-readable instructions that perform the functions described herein, the program being stored in any of the above-described non-transitory electronic memories and/or a hard disk drive, CD, DVD, FLASH drive or any other known storage media. Further, the computer-readable instructions may be provided as a utility application, background daemon, or component of an operating system, or combination thereof, executing in conjunction with a processor, such as a Xenon processor from Intel of America or an Opteron processor from AMD of America and an operating system, such as Microsoft VISTA, UNIX, Solaris, LINUX, Apple, MAC-OS and other operating systems known to those skilled in the art.

The images generated by the circuit 7 via a reconstruction process are stored in the memory 8, and/or displayed on the display 9. As one of ordinary skill in the art would recognize, the memory 8 can be a hard disk drive, CD-ROM drive, DVD drive, FLASH drive, RAM, ROM or any other electronic storage known in the art. The display 9 can be implemented as an LCD display, CRT display, plasma display, OLED, LED or any other display known in the art. As such, the descriptions of the memory and the display provided herein are merely exemplary and in no way limit the scope of the present advancements.

While certain embodiments have been described, these embodiments have been presented by way of example only, and are not intended to limit the scope of the inventions. Indeed the novel methods and systems described herein may be embodied in a variety of other forms; furthermore, various omissions, substitutions, and changes in the form of the methods and systems described herein may be made without departing from the spirit of the inventions. The accompanying claims and their equivalents are intended to cover such forms or modifications as would fall within the scope and spirit of the inventions.

The invention claimed is:

1. A method of performing spectral reconstruction for a region of interest (ROI) of an object, the method comprising:
    designating the ROI within the object, the ROI being located within a scan field of view (FOV) of a computed tomography (CT) scanner having an X-ray source;
    performing a first scan of the object using a first peak voltage of the X-ray source and a first filter, to obtain a first data set, the first filter corresponding to the scan FOV;
    performing a second scan of the object using a second peak voltage of the X-ray source and a second filter, to obtain a second data set, the second filter resulting in a FOV smaller than the scan FOV and including the ROI; and
    performing spectral reconstruction within the ROI using the first and second data sets to obtain spectral images of the ROI.

2. The method of claim 1, wherein the step of performing reconstruction further comprises generating a full energy-integrating image within the scan FOV.

3. The method of claim 1, further comprising displaying the spectral images of the ROI.

4. The method of claim 1, further comprising switching from the first filter to the second filter after the first scan but before the second scan.

5. The method of claim 1, wherein the first and second filters are bowtie filters.

6. An apparatus for performing spectral reconstruction for a region of interest (ROI) of an object, the apparatus being communicatively connected to a computed tomography (CT) scanner having an X-ray source, the apparatus comprising:
   a circuit configured to
   receive designation of the ROI within the object, the ROI being located within a scan field of view (FOV) of the computed tomography (CT) scanner;
   cause the CT scanner to perform a first scan of the object using a first peak voltage of the X-ray source and a first filter, to obtain a first data set, the first filter corresponding to the scan FOV;
   cause the CT scanner to perform a second scan of the object using a second peak voltage of the X-ray source and a second filter, to obtain a second data set, the second filter resulting in a FOV smaller than the scan FOV and including the ROI; and
   perform spectral reconstruction within the ROT using the first and second data sets to obtain spectral images of the ROI.

7. A method of performing spectral reconstruction for a region of interest (ROI) of an object, the method comprising:
   designating the ROI within the object, the ROI being located within a scan field of view (FOV) of a dual-source, dual detector computed tomography (CT) scanner, the CT scanner having a first X-ray source and a second X-ray source;
   setting a first peak voltage and a first FOV for the first X-ray source;
   setting a second peak voltage and a second FOV for the second X-ray source, the second FOV being smaller than the first FOV and including the ROI;
   performing a scan of the object using the first and second X-ray sources to obtain first and second data sets, respectively; and
   performing spectral reconstruction within the ROI using the first and second data sets to obtain spectral images of the ROI.

8. The method of claim 7, wherein the step of performing reconstruction further comprises generating a full energy-integrating image within the scan FOV.

9. The method of claim 7, further comprising displaying the spectral images of the ROI.

10. The method of claim 7, wherein the CT scanner includes a first detector and a second detector, and the first and second detectors have different sizes.

11. An apparatus for performing spectral reconstruction for a region of interest (ROI) of an object, the apparatus being communicatively connected to a dual-source, dual detector computed tomography (CT) scanner, the CT scanner having a first X-ray source and a second X-ray source, the apparatus comprising:
   a circuit configured to
   receive designation of the ROI within the object, the ROI being located within a scan field of view (FOV) of the dual-source, dual detector CT scanner;
   set a first peak voltage and a first FOV for the first X-ray source;
   set a second peak voltage and a second FOV for the second X-ray source, the second FOV being smaller than the first FOV and including the ROI;
   cause the CT scanner to perform a scan of the object using the first and second X-ray sources to obtain first and second data sets, respectively; and
   perform spectral reconstruction within the ROI using the first and second data sets to obtain spectral images of the ROI.

* * * * *